United States Patent
Lin et al.

(10) Patent No.: US 7,993,343 B2
(45) Date of Patent: *Aug. 9, 2011

(54) EXTRACTABLE FILLER FOR INSERTING MEDICINE INTO VERTEBRAL BODY

(75) Inventors: Kwan Ku Lin, Pasadena, CA (US);
Philip S. Yuan, Fayetteville, NY (US)

(73) Assignee: Crosstrees Medical, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/674,088

(22) Filed: Feb. 12, 2007

(65) Prior Publication Data
US 2007/0129670 A1 Jun. 7, 2007

Related U.S. Application Data

(63) Continuation of application No. 10/949,217, filed on Sep. 27, 2004, now Pat. No. 7,175,629.

(30) Foreign Application Priority Data

Sep. 29, 2003 (TW) ................................ 92126916 A (51) Int. Cl.
*A61F 2/46* (2006.01)
*A61M 31/00* (2006.01)
(52) U.S. Cl. .......................... 606/86 R; 604/500; 604/60
(58) Field of Classification Search .............. 604/57–64, 604/93.01, 500, 502; 606/92–94, 86; 623/17.12
See application file for complete search history.

(56) References Cited

U.S. PATENT DOCUMENTS

| 4,488,549 A | 12/1984 | Lee et al. |
| 4,625,722 A | 12/1986 | Murray |
| 4,969,888 A | 11/1990 | Scholten et al. |
| 5,017,175 A * | 5/1991 | Klusmire .................. 452/38 |
| 5,054,492 A | 10/1991 | Scribner et al. |
| 5,108,404 A | 4/1992 | Scholten et al. |
| 5,549,679 A * | 8/1996 | Kuslich .................. 623/17.12 |
| 5,632,275 A | 5/1997 | Browne et al. |

(Continued)

FOREIGN PATENT DOCUMENTS

EP 1 495 729 A1 1/2005

(Continued)

OTHER PUBLICATIONS

International Search Report and Written Opinion for International Application PCT/US06/61207, mailed Oct. 5, 2007.

(Continued)

*Primary Examiner* — Theodore J Stigell
*Assistant Examiner* — Catherine N Witczak (57) ABSTRACT

An extractable device is used to insert a medicinal filling into a vertebral body. The device comprises a filling member and a pasty medicine. The filling member is made of a flexible and permeable wall and is provided with a holding portion and an injection port via which the pasty medicine is injected into the holding portion after the filling member is inserted into the vertebral body. The holding portion is provided with an opening which is releasably lashed by one end of one or more threads so as to make the opening leakproof. Upon completion of solidification of the pasty medicine in the holding portion of the filling member, other end of the thread is pulled to unlash the opening of the holding portion, thereby enabling the filling member to be extracted from the vertebral body so as to leave only the medicine in the vertebral body.

19 Claims, 11 Drawing Sheets

U.S. PATENT DOCUMENTS

| | | | |
|---|---|---|---|
| 5,744,958 | A | 4/1998 | Werne |
| 5,782,764 | A | 7/1998 | Werne |
| 5,827,289 | A | 10/1998 | Reiley et al. |
| 5,972,015 | A | 10/1999 | Scribner et al. |
| 5,976,186 | A | 11/1999 | Bao et al. |
| 6,048,346 | A | 4/2000 | Reiley et al. |
| 6,053,904 | A | 4/2000 | Scribner et al. |
| 6,066,154 | A | 5/2000 | Reiley et al. |
| 6,146,422 | A | 11/2000 | Lawson |
| 6,235,043 | B1 | 5/2001 | Reiley et al. |
| 6,241,734 | B1 | 6/2001 | Scribner et al. |
| 6,245,107 | B1 | 6/2001 | Ferree |
| 6,248,110 | B1 | 6/2001 | Reiley et al. |
| 6,402,784 | B1 | 6/2002 | Wardlaw |
| 6,440,138 | B1 | 8/2002 | Reiley et al. |
| 6,443,988 | B2 | 9/2002 | Felt et al. |
| 6,488,710 | B2 | 12/2002 | Besselink |
| 6,508,839 | B1 | 1/2003 | Lambrecht et al. |
| 6,533,817 | B1 | 3/2003 | Norton et al. |
| 6,558,390 | B2 | 5/2003 | Cragg |
| 6,575,919 | B1 | 6/2003 | Reiley et al. |
| 6,602,291 | B1 | 8/2003 | Ray et al. |
| 6,607,544 | B1 | 8/2003 | Boucher et al. |
| 6,632,235 | B2 | 10/2003 | Weikel et al. |
| 6,641,587 | B2 | 11/2003 | Scribner et al. |
| 6,645,213 | B2 | 11/2003 | Scribner et al. |
| 6,706,069 | B2 | 3/2004 | Berger |
| 6,712,819 | B2 | 3/2004 | Zucherman et al. |
| 6,716,216 | B1 | 4/2004 | Boucher et al. |
| 6,719,773 | B1 | 4/2004 | Boucher et al. |
| 6,726,691 | B2 | 4/2004 | Osorio et al. |
| 6,740,093 | B2 | 5/2004 | Hochschuler et al. |
| 6,923,813 | B2 | 8/2005 | Phillips et al. |
| 6,960,215 | B2 | 11/2005 | Olson, Jr. et al. |
| 6,979,341 | B2 | 12/2005 | Scribner et al. |
| 7,044,954 | B2 | 5/2006 | Reiley et al. |
| 7,081,122 | B1 | 7/2006 | Reiley et al. |
| 7,153,306 | B2 | 12/2006 | Ralph et al. |
| 7,166,121 | B2 | 1/2007 | Reiley et al. |
| 7,175,627 | B2 * | 2/2007 | Lin et al. .................... 606/86 R |
| 7,175,628 | B2 * | 2/2007 | Lin et al. .................... 606/86 R |
| 7,175,629 | B2 * | 2/2007 | Lin et al. .................... 606/86 R |
| 7,226,481 | B2 | 6/2007 | Kuslich |
| 7,241,303 | B2 | 7/2007 | Reiss et al. |
| 7,261,720 | B2 | 8/2007 | Stevens et al. |
| 7,465,318 | B2 | 12/2008 | Sennett et al. |
| 7,749,230 | B2 * | 7/2010 | Yuan et al. .................. 606/86 R |
| 2002/0026195 | A1 | 2/2002 | Layne et al. |
| 2003/0050644 | A1 | 3/2003 | Boucher et al. |
| 2004/0010260 | A1 | 1/2004 | Scribner et al. |
| 2004/0024410 | A1 | 2/2004 | Olson, Jr. et al. |
| 2004/0059417 | A1 * | 3/2004 | Smith et al. ................ 623/17.11 |
| 2004/0102774 | A1 | 5/2004 | Trieu |
| 2004/0106999 | A1 | 6/2004 | Mathews |
| 2004/0122455 | A1 | 6/2004 | Lin |
| 2004/0210297 | A1 | 10/2004 | Lin et al. |
| 2005/0065609 | A1 * | 3/2005 | Wardlaw .................... 623/17.12 |
| 2005/0090852 | A1 | 4/2005 | Layne et al. |
| 2005/0228397 | A1 | 10/2005 | Malandain et al. |
| 2005/0267483 | A1 | 12/2005 | Middleton |
| 2006/0079905 | A1 | 4/2006 | Beyar et al. |
| 2006/0155296 | A1 | 7/2006 | Richter |
| 2006/0229625 | A1 | 10/2006 | Truckai et al. |
| 2006/0247648 | A1 | 11/2006 | Serbousek |
| 2007/0129669 | A1 | 6/2007 | Lin et al. |
| 2007/0142765 | A1 | 6/2007 | Lin et al. |
| 2007/0156242 | A1 | 7/2007 | Lin et al. |
| 2008/0097511 | A1 | 4/2008 | Yuan et al. |
| 2009/0254132 | A1 | 10/2009 | Scribner et al. |
| 2011/0004312 | A1 | 1/2011 | Yuan et al. |

FOREIGN PATENT DOCUMENTS

| | | |
|---|---|---|
| EP | 1 495 730 A1 | 1/2005 |
| EP | 1 588 674 | 10/2005 |
| EP | 1 588 732 | 10/2005 |
| EP | 1 882 459 | 1/2008 |
| WO | WO 02/26170 A2 | 4/2002 |
| WO | WO 03/057088 A1 | 7/2003 |
| WO | WO 2009/036466 | 3/2009 |

OTHER PUBLICATIONS

European Office Action for EP 05794205.4, mailed Oct. 2, 2009.
Chinese Office Action for 200680043269.1, mailed Sep. 25, 2009.
International Search Report for PCT/US2005/031356, mailed Apr. 7, 2006.
Office Action for U.S. Appl. No. 11/674,085, mailed Nov. 4, 2009.
Office Action for U.S. Appl. No. 11/674,085, mailed Apr. 3, 2009.
Office Action for U.S. Appl. No. 11/674,085, mailed Apr. 22, 2008.
Office Action for U.S. Appl. No. 11/674,085, mailed Nov. 29, 2007.
Office Action for U.S. Appl. No. 11/674,085, mailed Jun. 11, 2007.
Office Action for U.S. Appl. No. 10/652,470, mailed Mar. 13, 2006.
Office Action for U.S. Appl. No. 11/574,562, mailed May 1, 2009.
Chinese Office Action for 200580037847.6, mailed Jan. 22, 2010.
Chinese Office Action for 200680043269.1, mailed May 7, 2010.
Final Office Action for U.S. Appl. No. 11/674,085, mailed Jun. 24, 2010.
International Search Report for PCT/US2006/026727, mailed Jan. 29, 2007.
Chinese Office Action for 200680029705.X, mailed Jul. 10, 2009.
Chinese Office Action for 200680029705.X, mailed Dec. 15, 2010.
Office Action for U.S. Appl. No. 11/562,803, mailed Jan. 7, 2009.
Office Action for U.S. Appl. No. 12/829,500, mailed Nov. 10, 2010.
U.S. Appl. No. 12/972,001, filed on Dec. 17, 2010.

* cited by examiner

EXTRACTABLE FILLER FOR INSERTING MEDICINE INTO VERTEBRAL BODY

FIELD OF THE INVENTION

The present invention relates generally to an instrument which is used in the restorative operation of vertebral body disorder. More specifically this surgical instrument can be used to insert a medical material into a vertebral body such that the instrument can be separated from the medical material and drawn out of the vertebral body, and the medical material solidifies in the vertebral body.

BACKGROUND OF THE INVENTION

The surgical treatment of vertebral body disorder can be generally attained by one of three methods, which include the hypodermic injection of medicine, the balloon-insertion of medicine, and the filler-insertion of medicine. For example, the U.S. Pat. Nos. 5,972,105; 6,066,154; and 6,248,110B1 disclose respectively a method for treating bone tissue disorders, such as osteoporosis and vertebral compression fractures. The method involves the use of a balloon (made by the Kyphon Crop., U.S.A.) by which the tissue is expanded to facilitate the inserting of the medicine. This balloon method is defective in design in that the medicine is apt to spread aimlessly in the tissue without boundary. Without containment, the medicine is not as effective and there is the possibility of injury to the surrounding tissues.

In order to prevent the drawbacks of the balloon method described above, the filler-insertion method is used to implant the medicine in vertebral body in such a way that the medicine is contained in the filler, and that both the medicine and the filler are implanted in the vertebral body. This filler-insertion method is often carried out in danger of the tissue rejection of the filler.

However, the aforesaid treatments do not focus on the retrieval of original spinal curvature, where the front end of the vertebra having vertebral compression fractures is relatively insufficiently supported, and the patient is apt to regain the vertebral collapse problem after the implantation surgery.

SUMMARY OF THE INVENTION

An extractable device for inserting a medicinal filling into a vertebral body, said device comprising:

a filling member comprising a flexible wall and provided with a holding portion, an injection port at one end of the holding portion, and an opening at another end of the holding portion;

one or more thread, each having one end for fastening releasably said opening of said holding portion in such a manner that said opening is leakproof; and a pasty medicine to be injected into said holding portion via said injection port of said filling member in the wake of a process for inserting said filling member into the vertebral body whereby said pasty medicine solidifies in said holding portion of said filling member;

said opening of said holding portion being unfastened at the time when other end of said threads is pulled by an external force, thereby enabling said filling member to be extracted from the vertebral body so as to leave only said medicine in the vertebral body, wherein said holding portion of said filling member is inflatable and is substantially tubular after being inflated, wherein cross sections perpendicular to a longitudinal axis of the holding portion are substantially elliptical and have increasing areas thereof along a direction from the injection port to the opening of the holding portion.

Preferably, said flexible wall is provided with a plurality of through holes and is permeable. Said flexible and permeable wall is of a one-layered or multi-layered construction.

Preferably, aid pasty medicine is a mixture of a liquid and a medicinal powdered substance or medicinal granular substance.

Preferably, the device of the present invention further comprises an injection tool for injecting said pasty medicine into said holding portion via said injection port.

Preferably, said injection tool comprises a guide tube and a syringe, wherein one end of said guide tube is connected to said injection port of said filling member and another end of said guide tube is connected to said syringe in which said pasty medicine is held, so that said pasty medicine is able to be injected into said holding portion of said filling member by said syringe via said injection port and said guide tube.

Preferably, the device of the present invention further comprises a working tube for inserting into said vertebral body, so that said filling member together with said guide tube can be inserted into said working tube and said filling member can be disposed in said vertebral body.

Preferably, said flexible wall is a folded double-layer tubular wall having an inner layer end and a folded double-layer end, wherein said injection port of said holding portion is provided at said inner layer end, and said opening of said holding portion is provided at said folded double-layer end, wherein said medicine is released from said filling member by pulling a free end of an outer layer of the double-layer tubular wall to retreat the folded double-layer end, after said opening of said holding portion being unfastened. More preferably, said one or more thread is between an inner layer and said outer layer of said double-layer tubular wall.

Preferably, said inner layer and said outer layer of said double-layer tubular wall are provided with a plurality of through holes and are permeable.

The present invention also discloses a method for implanting a solidified medicine into a vertebral body comprising:

inserting a filling member in a hole of a vertebral body, said filling member comprising a flexible and permeable wall and provided with a holding portion, an injection port at one end of the holding portion, and an opening at another end of the holding portion, wherein one or more thread is provided and each having one end fastening releasably said opening of said holding portion in such a manner that said opening is leakproof, wherein said holding portion of said filling member is inflatable and is substantially tubular after being inflated, wherein cross sections perpendicular to a longitudinal axis of the holding portion are substantially elliptical and have increasing areas thereof along a direction from the injection port to the opening of the holding portion;

injecting a pasty medicine into said holding portion via said injection port of said filling member, so that said holding portion is inflated and said pasty medicine solidifies in said holding portion of said filling member; and unfastening said opening of said holding portion by pulling other end of said threads, thereby enabling said filling member to be extracted from the vertebral body so as to leave only said solidified medicine in the vertebral body, wherein said solidified pasty medicine has a shape similar to that of the inflated holding portion, and a cross section having a greater area of said solidified medicine is closer to a cortical rim opposite to a pedicle of said vertebral body in comparison with a cross section having a smaller area of said solidified medicine.

Preferably, the method of the present invention further comprises fastening detachably an injection tool with said filling member, so that said pasty medicine is injected into said holding portion via said injection tool. More preferably, said injection tool comprises a guide tube and a syringe, wherein one end of said guide tube is connected to said injection port of said filling member and another end of said guide tube is connected to said syringe in which said pasty medicine is held, wherein said pasty medicine is injected into said holding portion of said filling member by said syringe via said injection port and said guide tube.

Preferably, the method of the present invention further comprises inserting a working tube in said hole of said vertebral body, and inserting said filling member together with said guide tube into said working tube, so that said filling member is disposed in said vertebral body.

The flexible wall of the filling member of the present invention is made of a biocompatible or biosynthetic material, such as rubber, elastic plastic, titanium, goat intestine, and the like. The flexible wall is provided with a plurality of pores and is therefore permeable. The flexible wall can be formed into an object in the form of sac, bag, ball, cylinder or rectangular column integrally or by joining separate pieces.

The filling member of the present invention may contain a ray imaging material, such as a metal wire, by which the precise position of the filling member can be easily located by a ray imaging system, such as an X-ray machine.

The flexible wall of the filling member of the present invention may be of a one-layered or multi-layered construction, depending on the particle size and the viscosity of the medicine. If the particle size of the medicine is relatively large, the flexible wall is preferably of a two-layered construction. If the viscosity of the medicine is relatively high, the flexible wall is also preferably of a two-layered construction. On the other hand, the flexible wall is preferably of a three-layered or four-layered construction under the circumstances that the particle size of the medicine is relatively small and that the viscosity of the medicine is relatively lower.

The features and the advantages of the present invention will be more readily understood upon a thoughtful deliberation of the following detailed description of the preferred embodiments of the present invention with reference to the accompanying drawings.

DETAILED DESCRIPTION OF THE PREFERRED EMBODIMENTS

Figure 1:
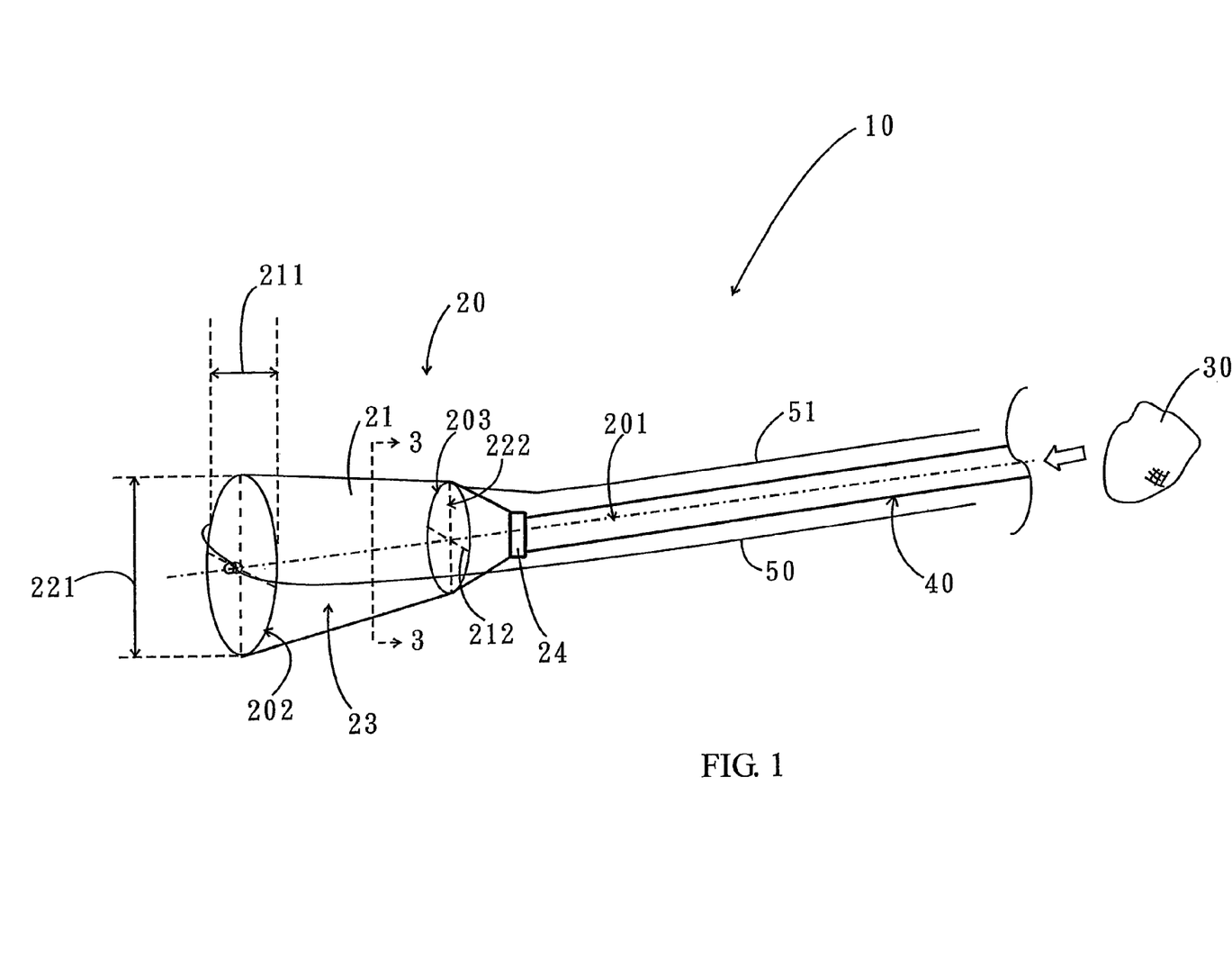
FIG. 1 shows a schematic view of an extractable filler of the present invention.

As shown in FIG. 1, an extractable filler 10 embodied in the present invention comprises a filling member 20, a pasty medicine 30, a guide tube 40, and two threads 50 and 51. The filling member 20 is formed of a flexible wall 21 and is provided with a holding portion 23 and an injection port 24. The flexible wall 21 may be made of rubber or a flexible plastic material with perforated holes. The pasty medicine 30 is injected into the holding portion 23 via the guide tube 40 and the injection port 24. The dotted line 3-3 shows a direction in which a section of the filling member 20 is taken. The holding portion 23 has a shape similar to a cone with a longitudinal axis 201, wherein two cross sections 202 and 203 perpendicular to the longitudinal axis 201 are elliptical. The cross section 202 has a short diameter 211 and a long diameter 221, and the cross section 203 has a short diameter 212 and a long diameter 222, wherein the short diameter 211 and the long diameter 221 are longer than the short diameter 212 and the long diameter 222, respectively. When the filling member 20 is inserted in a collapsed vertical body, the cross section 202 is at a position closer to a cortical rim opposite to a pedicle of said vertebral body and the cross section 203 is at a position near to the cortical rim close to the pedicle of said vertebral body. Preferably, the long diameters 221 and 222 are in the same direction of the vertebral column.

Figure 2A:
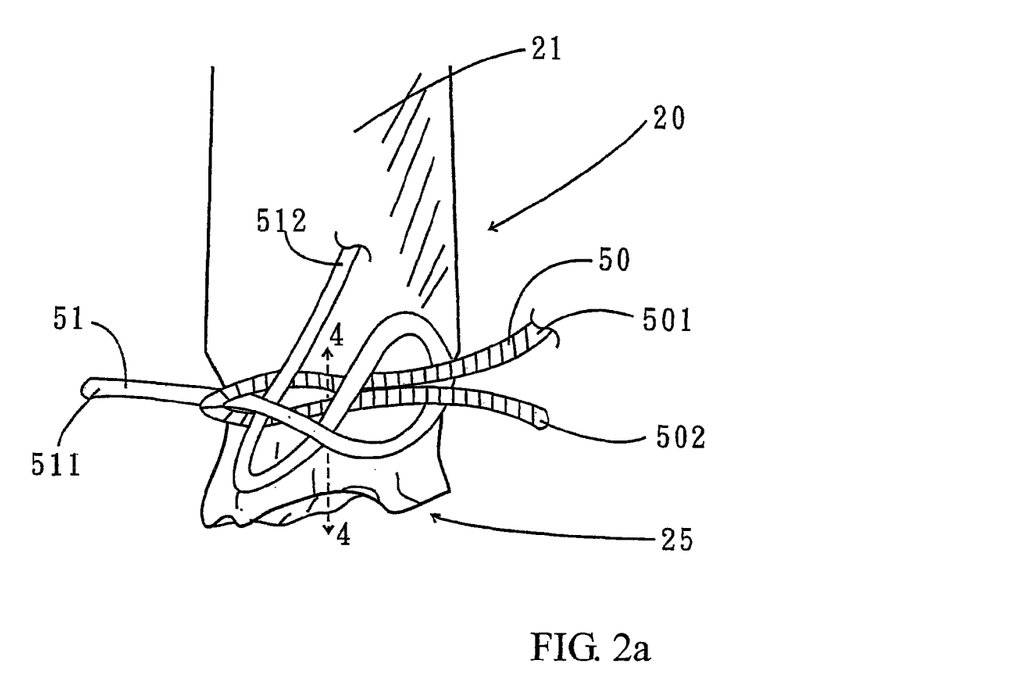
FIGS. 2a and 2b are schematic views illustrating the lashing of the opening of the holding portion of the filling member of the present invention.
Figure 2B:
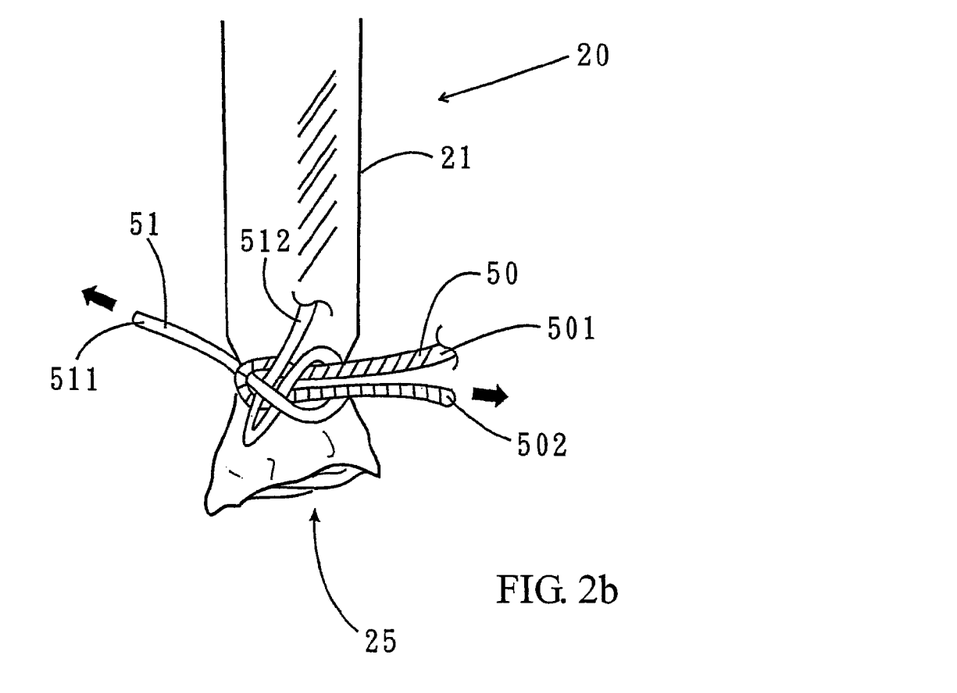

As shown in FIGS. 2a and 2b, the holding portion 23 of the filling member 20 is provided with an opening 25 opposite to the injection port 24 of the filling member 20. The opening 25 is lashed by two threads 50 and 51. The first thread 50 has a first end 501 and a second end 502, while the second thread 51 has a first end 511 and a second end 512. The two threads 50 and 51 are in fact fastened releasably to the flexible wall 21 near the opening 25. The way by which they are fastened together is not shown in the drawing.

The opening 25 of the holding portion 23 of the filling member 20 is securely tied up to prevent the medicine 30 from leaking out of the holding portion 23 by means of the two threads 50 and 51 which are releasably entangled in such a manner that the first end 511 of the second thread 51 is wound around the first thread 50. Upon completion of the winding process, the flexible wall 21 surrounding the opening 25 is located in a position between the two threads 50 and 51, as indicated by a dotted line 4-4 in FIG. 2a. Thereafter, both ends 501 and 502 of the first thread 50, and the first end 511 of the second thread 51 are respectively pulled rightward and leftwards at the same time, as illustrated in FIG. 2b. As a result, the opening 25 of the filling member 20 is leakproof.

Figure 3A:
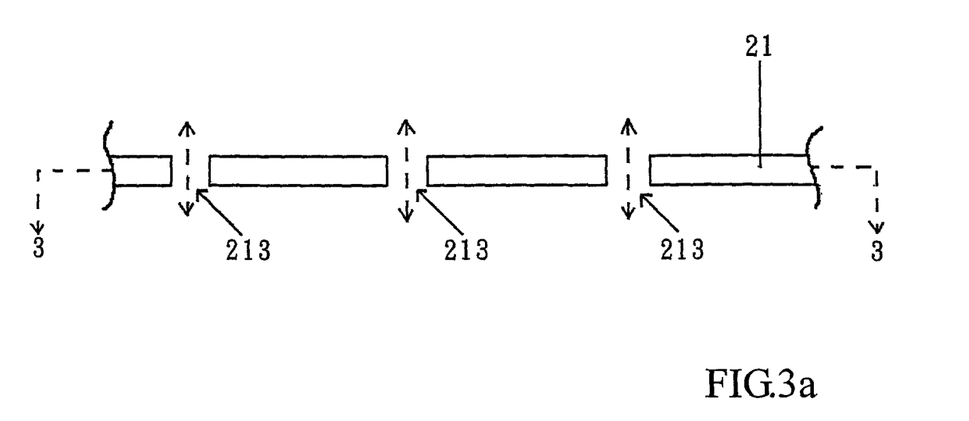
FIG. 3a shows a longitudinal sectional view of a one-layered wall of the filling member of the present invention.
Figure 3B:
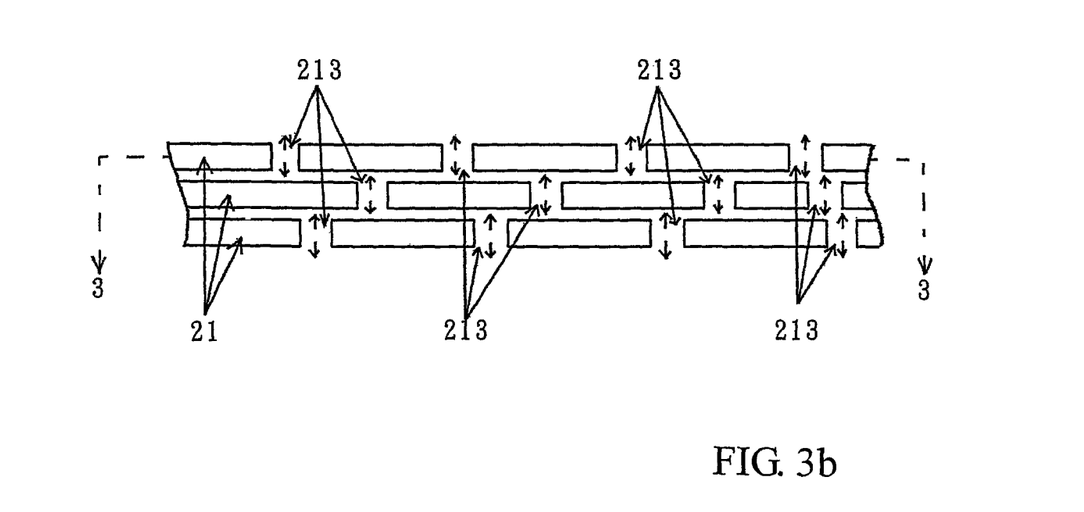
FIG. 3b shows a longitudinal sectional view of a multi-layered wall of the filling member of the present invention.

The flexible wall 21 of the filling member 20 is of a one-layered construction, as shown in FIG. 3a, or of a multi-layered construction, as shown in FIG. 3b. The flexible wall 21 is provided with a plurality of pores 213 permeable to fluids. If the flexible wall 21 is of a multi-layered construction, the flexible walls 21 are laminated in such a way that the pores 213 are not corresponding in location to slow down the passage of the fluids.

Figure 4A:
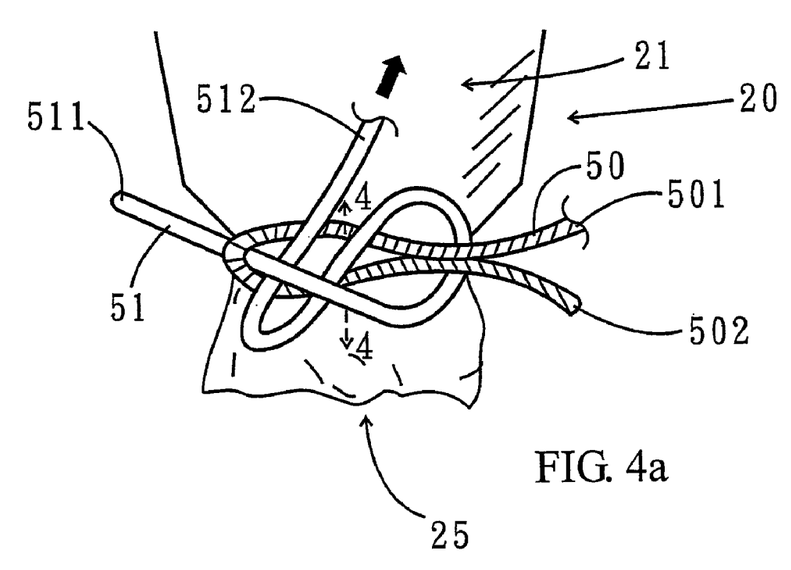
FIGS. 4a and 4b are schematic views illustrating the unlashing of the opening of the holding portion of the filling member of the present invention upon completion of the injection of the medicine into the holding portion of the filling member.
Figure 4B:
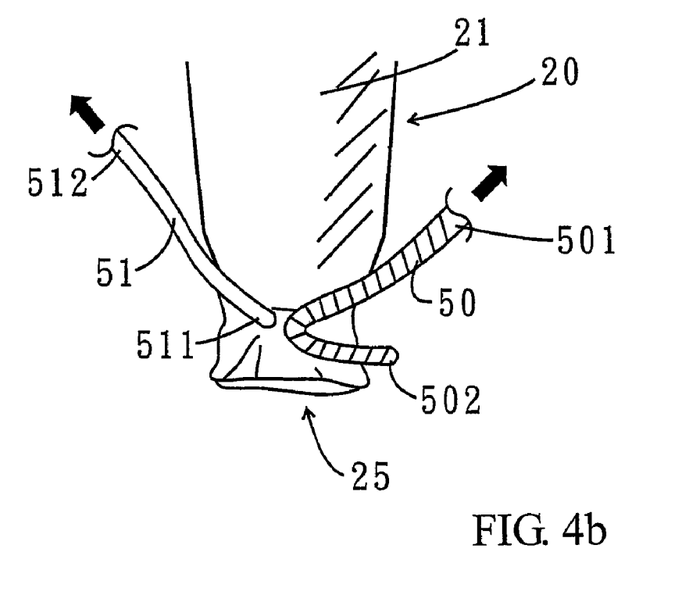

The opening 25 of the filling member 20 is untied when the second end 512 of the second thread 51 is pulled upward as indicated by an arrow in FIG. 4a. As a result, the two threads 50 and 51 become loosened. Thereafter, the first end 501 of the first thread 50 and the second end 512 of the second thread 51 are respectively pulled in a direction away from the opening 25 of the filling member 20, as illustrated in FIG. 4b. The opening 25 is thus unfastened completely.

Figure 5A:
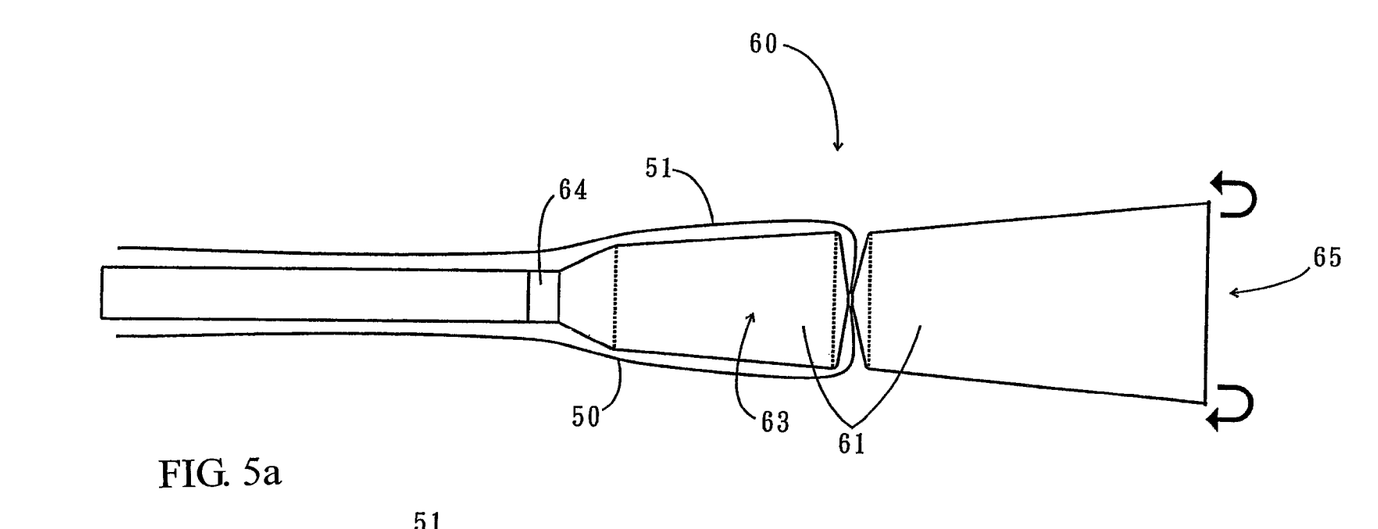
FIGS. 5a and 5b are schematic views illustrating a process in which a double-layer wall of the holding portion of the filling member of the present invention is formed.
Figure 5B:
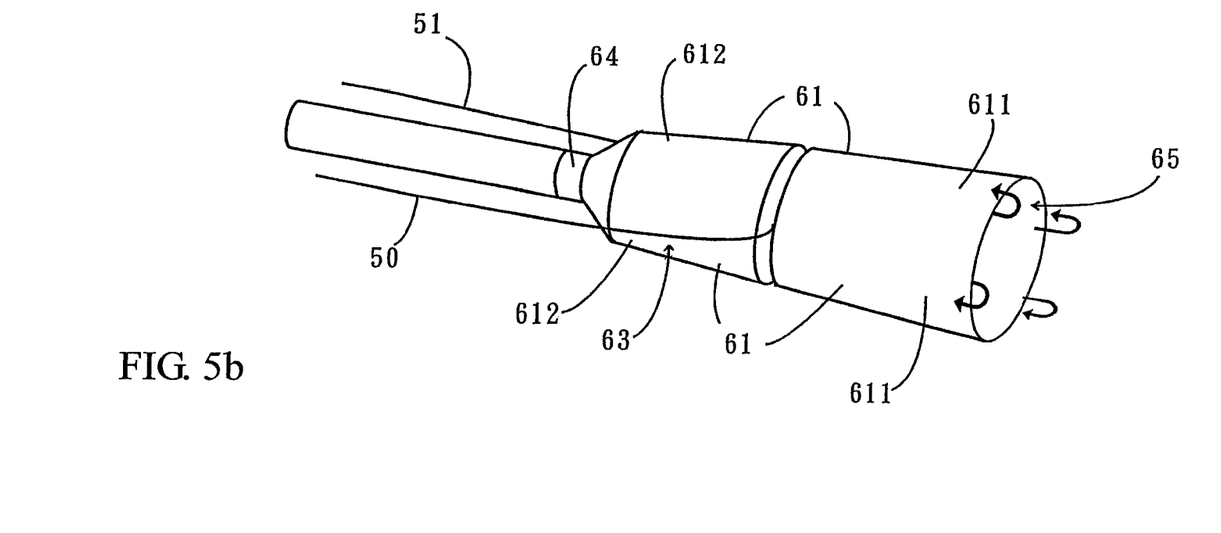
Figure 5C:
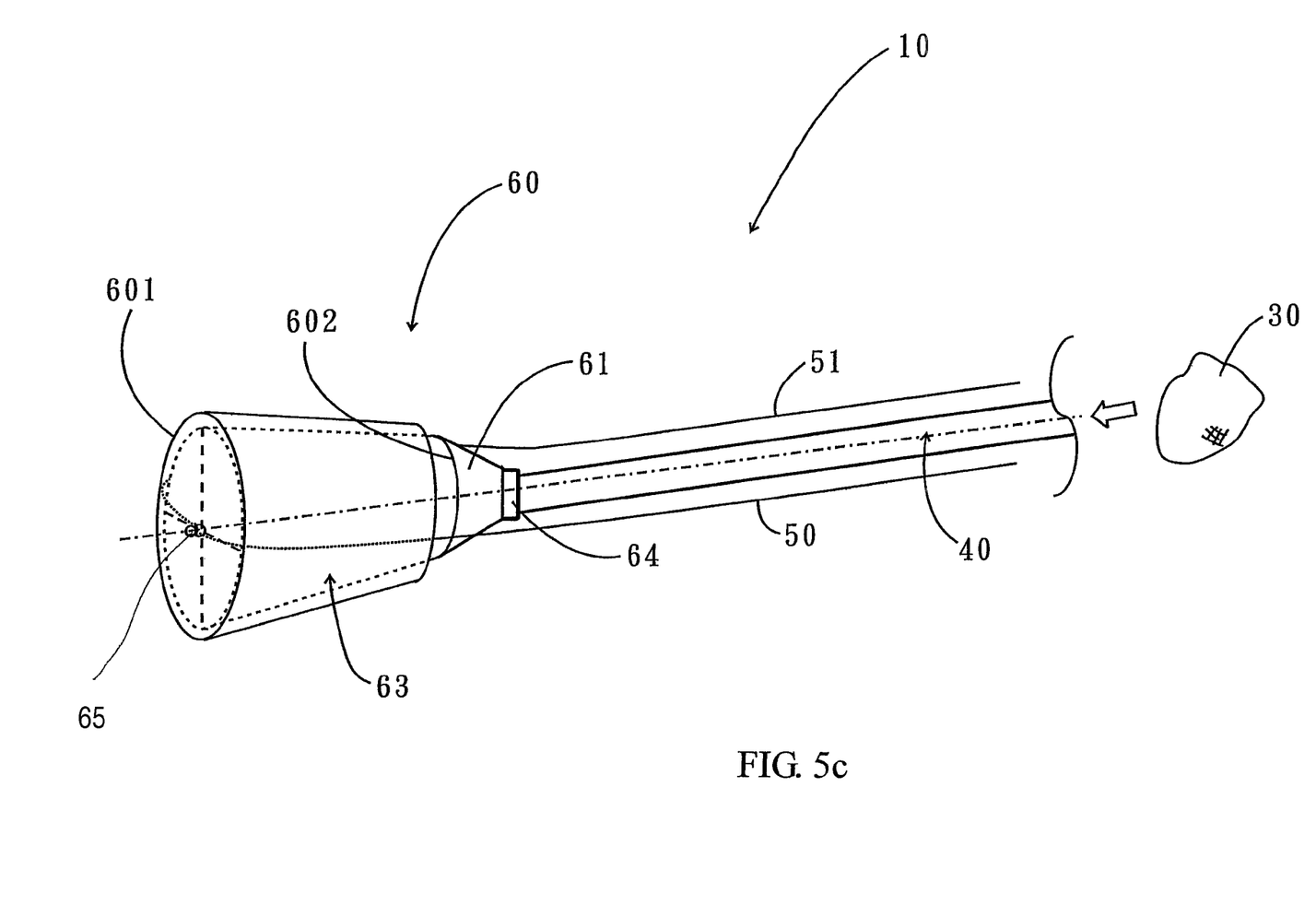
FIG. 5c is a schematic view of the extractable filler shown in FIGS. 5a and 5b after the double-layer wall of the holding portion of the filling member is formed.

A further embodiment of the present invention is shown in FIGS. 5a, 5b and 5c, which is similar to the embodiment shown in FIGS. 1 to 4b, except that a filling member 60 is formed of a double-layer wall 61 and the first thread 50 and second thread 51 are located between an inner layer 612 and an outer layer 611 of the double-layer wall 61. As shown in FIGS. 5a and 5b, a flexible and permeable tubular wall having an injection port 64 at one end is tied at an intermediate point thereof by the threads 50 and 51 at the beginning. The lower portion 611 of the tubular wall (will become an outer layer) is then rolled up, so that it is inside out and covering up the threads 50 and 51 and the upper portion 612 of the tubular wall (will become an inner layer). The rolled-up end of said double-layer wall 61 is provided with an opening 65 of the holding portion 63, which is lashed by the two threads 50 and 51. The holding portion 63 as shown in FIG. 5c has a conic shape similar to the embodiment shown in FIG. 1. The opening 65 can be unfastened by pulling the threads 50 and 51 the same way as shown in FIGS. 4a and 4b.

Figure 6A:
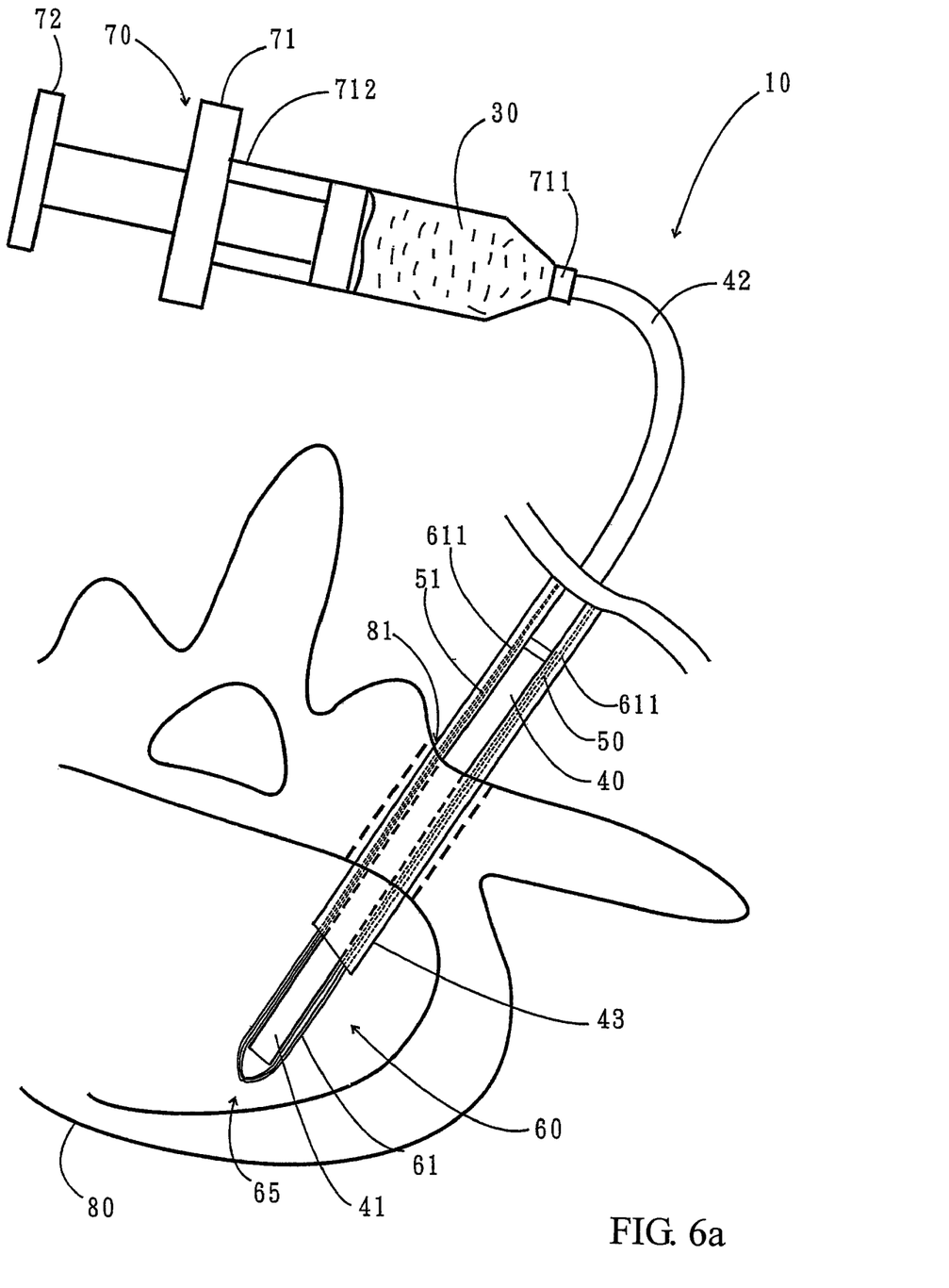
FIGS. 6a to 6c are sectional schematic views of the present invention at work.
Figure 6B:
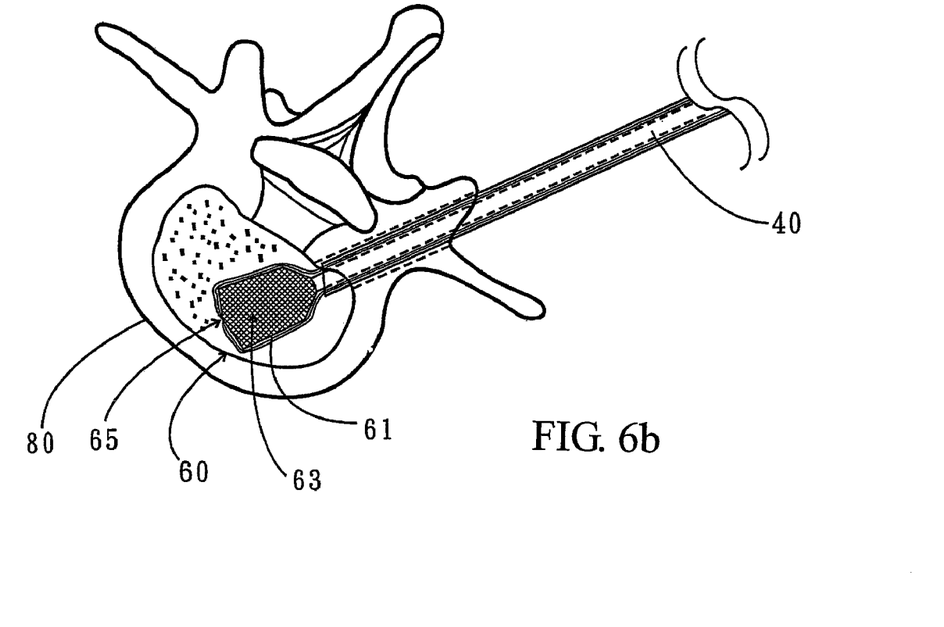
Figure 6C:
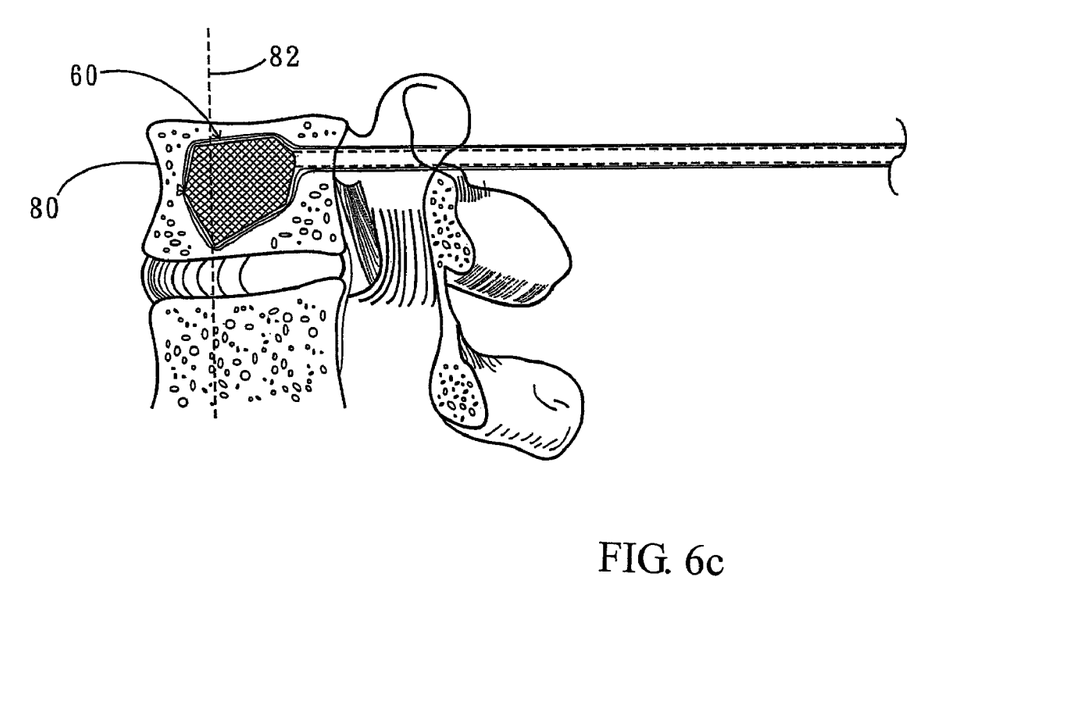

As shown in FIGS. 6a to 6c, the filling member 60 of the extractable filler 10 is inserted into a hole 81 formed on a vertebral body 80, wherein a working tube 43 is inserted into the hole 81 in advance to accommodate the guide tube 40, the threads 50 and 51 and the free end of the outer layer 611 of the double-layer wall 61 of the filling member 60. The pasty medicine 30 is then injected into the holding portion 63 of the filling member 60 by a syringe 70 in conjunction with the guide tube 40. The guide tube 40 has one end 41 in the holding portion 63, and another end 42 connected to one end 711 of a barrel 71 of the syringe 70. A plunger 72 is slidably inserted into another end 712 of the barrel 71 in which the pasty medicine 30 is contained. The filling member 60 is thus inflated by the medicine 30, as shown in FIGS. 6b and 6c, wherein the greater cross section thereof is at a position closer to a cortical rim opposite to a pedicle of said vertebral body and the smaller cross section thereof is at a position near to the cortical rim close to the pedicle of said vertebral body. Preferably, the long diameters of the elliptical cross sections of the pasty medicine 30 are in the same direction of the vertebral column indicated by a dot line 82 in FIG. 6c, thereby there may be enough room in the vertical body 80 for implanting two pasty medicines 30.

The pasty medicine 30 is a mixture of a liquid and one or more kinds of vertebral body drugs in the form of powder, granule, or colloid. The pasty medicine 30 is capable of solidification.

Upon completion of the solidification of the pasty medicine 30 in the vertebral body 80, the filling member 60 must be extracted from the hole 81 of the vertebral body 80, so as to leave only the medicine 30 in the vertebral body 80 to prevent the rejection of the filling member 60 by the human body. The extraction of the filling member 60 from the hole 81 of the vertebral body 80 involves a first step in which the second end 512 of the second thread 51 is pulled upward as indicated by an arrow in FIG. 4a. As a result, the two threads 50 and 51 become loosened. Thereafter, the first end 501 of the first thread 50 and the second end 512 of the second thread 51 are respectively pulled in a direction away from the opening 65 of the filling member 60, as illustrated in FIG. 4b. The opening 65 is thus unfastened completely.

Figure 7A:
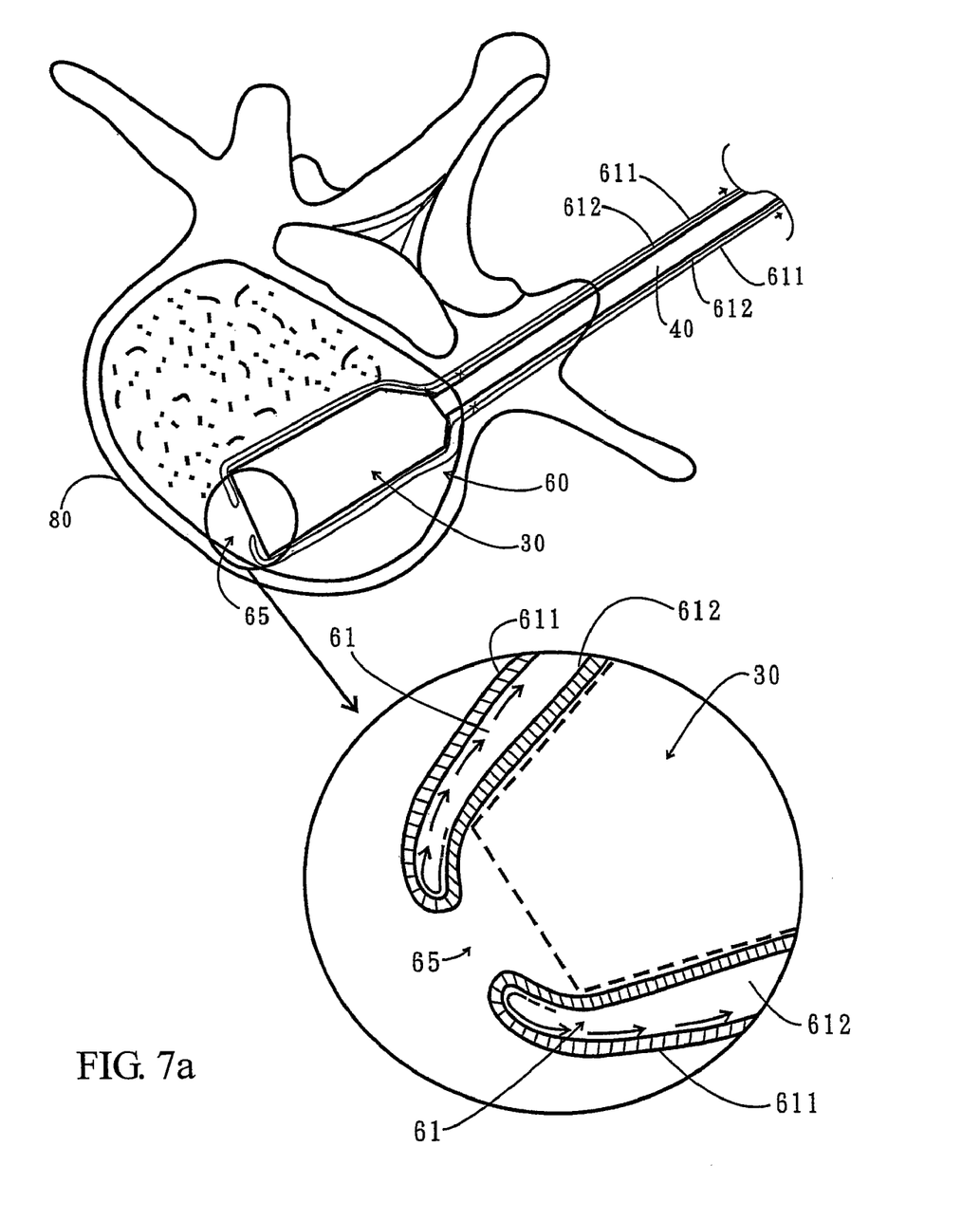
FIGS. 7a and 7b are sectional schematic views illustrating the process in which the filling member of the present invention is extracted from the vertebral body.
Figure 7B:
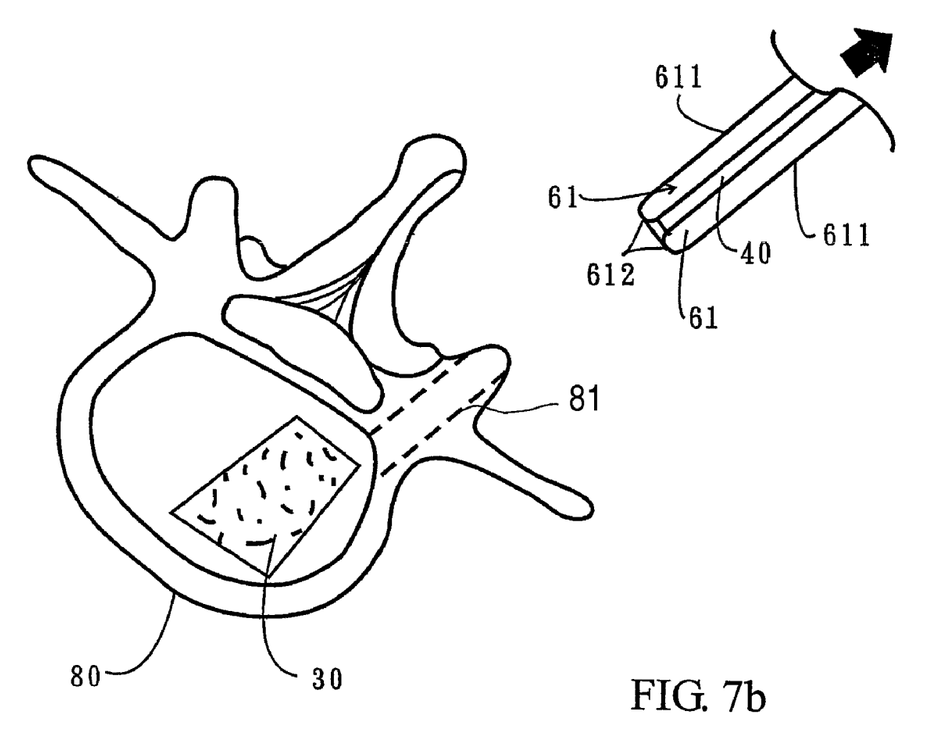

After the opening 65 being unfastened, the rolled-up double-layer end is retreated from the solidified medicine 30 by pulling a free end of the outer layer 611 of the double-layer wall 61, while one end of the inner layer 612 is connected to the guide tube 40 as an injection port of said holding portion of the said filling member 60, whereby said solidified medicine 30 is released from said filling member 60 and is disposed in the vertebral body 80, as shown in FIGS. 7a and 7b. The filling member and the guide up 40 are pulled from the hole 81 of the vertebral body 80, so as to leave only said solidified medicine 30 in the vertebral body 80.

Figure 8A:
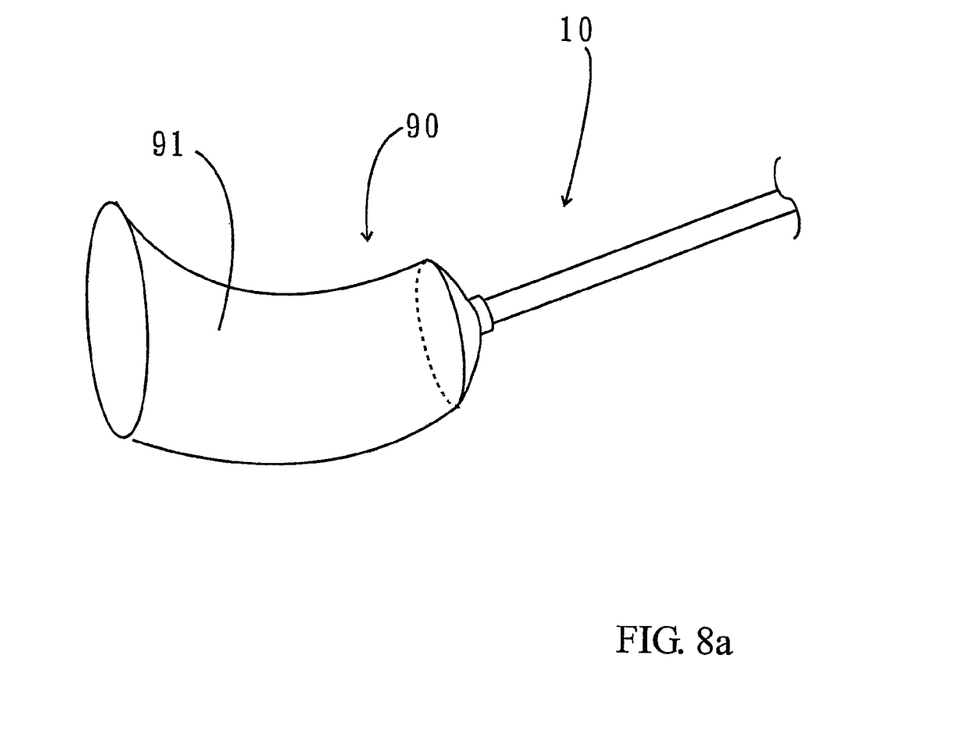
FIGS. 8a and 8b are schematic views illustrating that the holding portion of the filling member of the present invention has a curved profile.
Figure 8B:
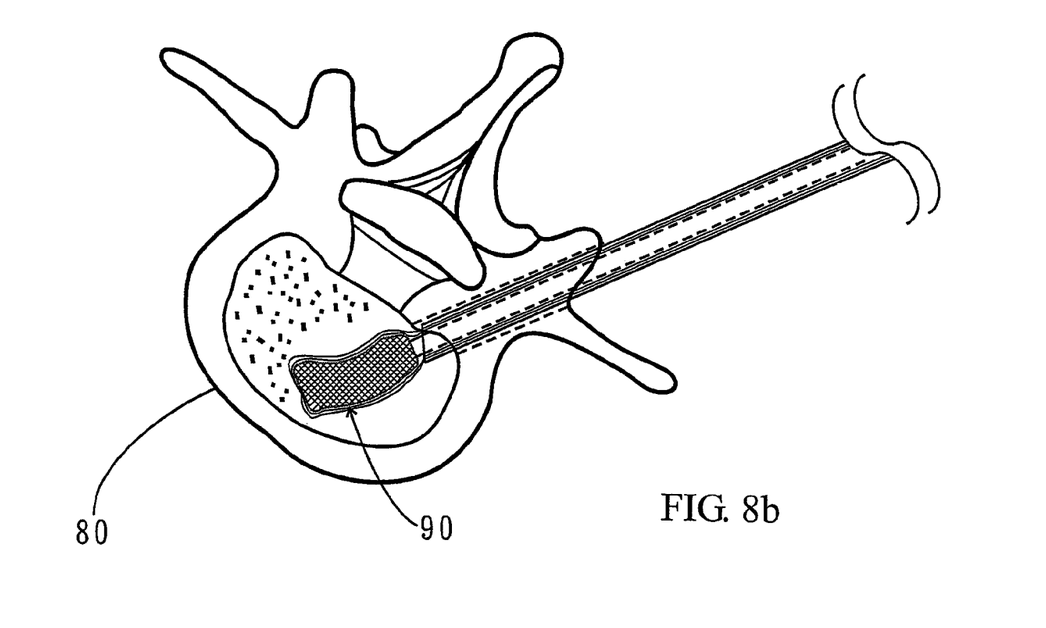

As shown in FIGS. 8a and 8b, the flexible wall 91 of the filling member 90 of the extractable filler 10 of the present invention may have a curved profile. Accordingly, the pasty medicine injected into the filling member 90 in the vertebral body will also has a curved profile.

The embodiments of the present invention described above are to be regarded in all respects as being illustrative and nonrestrictive. Accordingly, the present invention may be embodied in other specific forms without deviating from the spirit thereof. The present invention is therefore to be limited only the scopes of the following claims.

The invention claimed is:

1. An extractable device, comprising:
   a flexible container having a proximal injection port configured to receive a solidifiable medicinal filling, and a previously created releasably closable distal opening configured to selectively allow delivery of the filling into a vertebral body outside of the container; and
   at least one releasable thread configured to releasably close the distal opening to contain the filling within the container prior to solidification, and configured to allow the distal opening to reopen without permanently severing the flexible container to enable the delivery of the filling into the vertebral body outside of the container after at least partial solidification;
   the flexible container having a first configuration, a second configuration and a third configuration, when the flexible container is in the second configuration, the flexible container is substantially tubular, when the flexible container is in the third configuration, the distal opening of the flexible container is open and the flexible container is disposed at least partially within the vertebral body, the proximal injection port having a substantially constant size when the flexible container is in the first configuration, the second configuration, and the third configuration.

2. The device of claim 1, in which the flexible container is at least one of permeable or hermetic.

3. The device of claim 1, in which the thread is releasable upon application of at least one of an external pulling force or an external pushing force.

4. The device of claim 1, in which the flexible container comprises a single-layered wall.

5. The device of claim 1, in which the flexible container comprises a multi-layered wall.

6. The device of claim 1, in which the flexible container is formed of a plurality of threads.

7. The device of claim 1, in which the flexible container is formed of a plurality of threads by weaving.

8. The device of claim 1, further comprising:
   an injection tool configured to inject the solidifiable medicinal filling into the device through the proximal injection port.

9. The device of claim 8, in which the injection tool comprises a guide tube connected to the proximal injection port.

10. The device of claim 1, in which the flexible container comprises a folded double-layer tubular wall having a proximal inner layer end and a distal folded double layer end, the delivery of the filling follows pulling a free end of an outer layer of the double-layer tubular wall to retreat the distal folded double-layer end, after the distal opening of the flexible container has been reopened.

11. The device of claim 10, in which at least one releasable thread is between an inner layer and the outer layer of the double-layer tubular wall.

12. The device of claim 10, in which an inner layer and the outer layer of the double-layer tubular wall include a plurality of through holes and are permeable.

13. The device of claim 1, in which the at least one releasable thread has a length sufficient to extend from a location within the animal tissue to a location outside the vertebral body.

14. The device of claim 1, in which, when the flexible container is in the second configuration, the flexible container includes a first portion with cross sectional areas that increase continuously at a first rate, and a second portion with cross sectional areas that increase continuously at a second rate, the first rate being greater than the second rate.

15. The device of claim 1, in which the flexible container has a length smaller than a length of the vertebral body, when the flexible container is in the second configuration.

16. The device of claim 1, in which, when the flexible container is in the second configuration, the flexible container is substantially tubular with cross sectional areas that increase from the proximal injection port to the distal opening.

17. An extractable device, comprising:
a flexible container having a proximal inlet configured to receive a solidifiable medicinal filling and a previously created releasably closable distal outlet configured to allow subsequent delivery of solidified filling into a vertebral body; and
at least one releasable thread configured to prevent leakage of the filling from the container without permanently severing the flexible container;
the flexible container having a first configuration, a second configuration and a third configuration, when the flexible container is in the second configuration, the flexible container is substantially tubular, when the flexible container is in the third configuration, the distal opening of the flexible container is open and the flexible container is disposed at least partially within the vertebral body, the proximal inlet having a substantially constant size when the flexible container is in the first configuration, the second configuration, and the third configuration.

18. The device of claim 17, in which, when the flexible container is in the second configuration, the flexible container includes a first portion with cross sectional areas that increase continuously at a first rate, and a second portion with cross sectional areas that increase continuously at a second rate, the first rate being greater than the second rate.

19. The device of claim 17, in which, when the flexible container is in the second configuration, the flexible container is substantially tubular with cross sectional areas that increase from the proximal inlet to the distal outlet.

* * * * *